United States Patent
Kim et al.

(10) Patent No.: US 10,088,493 B2
(45) Date of Patent: Oct. 2, 2018

(54) METHOD FOR CELL-FREE PROTEIN SYNTHESIS INVOLVED WITH PH CONTROL WITH AMINO ACID DECARBOXYLASE

(71) Applicant: THE INDUSTRY & ACADEMIC COOPERATION IN CHUNGNAM NATIONAL UNIVERSITY, Daejeon (KR)

(72) Inventors: Dong-Myung Kim, Daejeon (KR); Taek Jin Kang, Seoul (KR); Ho-Cheol Kim, Gyeonggi-do (KR); Ki Baek Lee, Gyeonggi-do (KR)

(73) Assignee: THE INDUSTRY & ACADEMIC COOPERATION IN CHUNGNAM NATIONAL UNIVERSITY, Daejeon (KR)

( * ) Notice: Subject to any disclaimer, the term of this patent is extended or adjusted under 35 U.S.C. 154(b) by 0 days.

(21) Appl. No.: 15/374,168

(22) Filed: Dec. 9, 2016

(65) Prior Publication Data

US 2017/0089931 A1    Mar. 30, 2017

Related U.S. Application Data

(63) Continuation-in-part of application No. PCT/KR2015/005910, filed on Jun. 12, 2015.

(30) Foreign Application Priority Data

Jun. 12, 2014 (KR) ........................ 10-2014-0071736

(51) Int. Cl.
| | |
|---|---|
| *C12P 7/48* | (2006.01) |
| *G01N 33/84* | (2006.01) |
| *C07K 1/02* | (2006.01) |
| *C12P 21/02* | (2006.01) |
| *G01N 33/68* | (2006.01) |

(52) U.S. Cl.
CPC ............... *G01N 33/84* (2013.01); *C07K 1/02* (2013.01); *C12P 21/02* (2013.01); *C12Y 401/01* (2013.01); *G01N 33/6845* (2013.01)

(58) Field of Classification Search
None
See application file for complete search history.

(56) References Cited

U.S. PATENT DOCUMENTS

| | | | | |
|---|---|---|---|---|
| 8,367,371 | B2* | 2/2013 | Tajima | C12N 9/88 435/41 |
| 2004/0131870 | A1* | 7/2004 | Ketelson | A61L 12/08 428/474.4 |
| 2009/0100536 | A1* | 4/2009 | Adams | A01N 25/34 800/260 |
| 2018/0028474 | A1* | 2/2018 | Turano | C12N 15/8279 |

FOREIGN PATENT DOCUMENTS

| | | |
|---|---|---|
| KR | 10-0733712 B1 | 6/2007 |
| KR | 10-0749053 B1 | 8/2007 |
| KR | 10-1202797 B1 | 11/2012 |
| KR | 10-1229849 B1 | 2/2013 |

OTHER PUBLICATIONS

Park, Ji Yeong, Graduate Thesis of Chungnam National University(Master), High-Throughput Screening of Glycosyltransferase in a Cell-Free Protein Synthesis System, 2012. See pp. 26-47.
Kim, T.-W., et al., "A Highly Efficient and Economical Cell-free Protein Synthesis System Using the S12 Extract of *Escherichia coli*" Biotechnology and Bioprocess Engineering, 2008. vol. 13, pp. 464-469, DOI/10.1007/s12257-008-0139-8 See the entire document.
Shimizu, Yoshihiro et al., "Cell-free translation reconstituted with purified components", 2001, Nature Biotechnology, 19(8): 751-755.
Tae-Wan Kim et. al, "Simple procedures for the construction of a robust and cost-effective cell-free protein synthesis system", 2006, Journal of Biotechnology, 126(4): 554-561.
Kara A. Calhoun et. al, "An Economical Method for Cell-Free Protein Synthesis using Glucose and Nucleoside Monophosphates", 2005, Biotechnology Progress, 21(4):1146-1153.
Ho-Cheol Kim et. al., "Prolonged production of proteins in a cell-free protein synthesis system using polymeric carbohydrates as an energy source", 2011, Process Biochemistry, 46(6): 1366-1369.

* cited by examiner

*Primary Examiner* — Hope Robinson
(74) *Attorney, Agent, or Firm* — The PL Law Group, PLLC

(57) ABSTRACT

A method for cell-free protein synthesis is characterized in that pH is controlled by using an enzyme. For example, by using an amino acid decarboxylase, the pH is controlled according to removal of hydrogen ions that are produced during regeneration of ATP. The method for cell-free protein synthesis of the present invention has an advantage that not only the expression amount of protein is enhanced but also the expressed protein can be directly used for activity analysis without undergoing any separation or purification.

6 Claims, 13 Drawing Sheets

Specification includes a Sequence Listing.

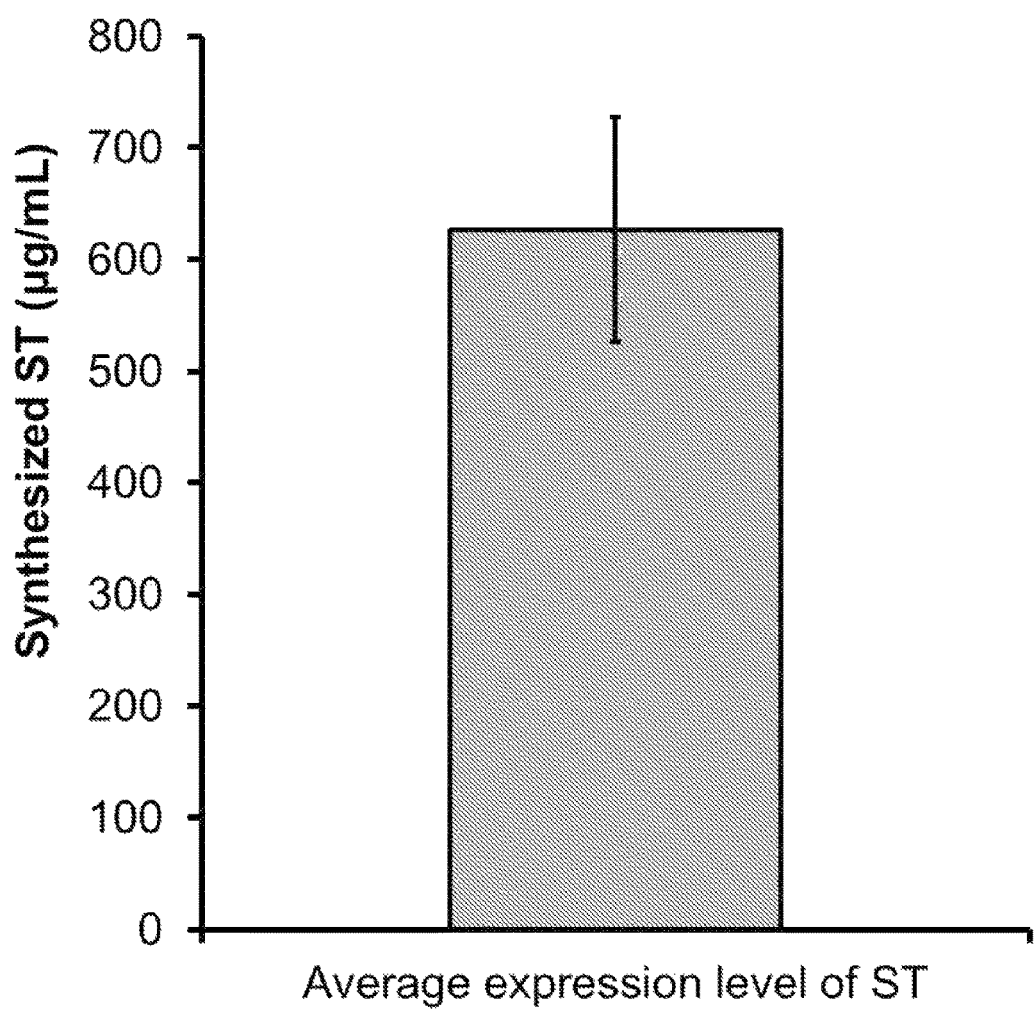

SEQUENCE LISTING

<160> NUMBER OF SEQ ID NOS: 10

<210> SEQ ID NO 1
<211> LENGTH: 466
<212> TYPE: PRT
<213> ORGANISM: Escherichia coli

<400> SEQUENCE: 1

```
Met Asp Lys Lys Gln Val Thr Asp Leu Arg Ser Glu Leu Leu Asp Ser
1               5                   10                  15

Arg Phe Gly Ala Lys Ser Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
    130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320
```

```
Ala Gly Gln Val Ile Ala Gln Tyr Tyr Glu Phe Leu Arg Leu Gly Arg
            325                 330                 335

Glu Gly Tyr Thr Lys Val Gln Asn Ala Ser Tyr Gln Val Ala Ala Tyr
        340                 345                 350

Leu Ala Asp Glu Ile Ala Lys Leu Gly Pro Tyr Glu Phe Ile Cys Thr
            355                 360                 365

Gly Arg Pro Asp Glu Gly Ile Pro Ala Val Cys Phe Lys Leu Lys Asp
370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
            405                 410                 415

Asp Ile Val Val Met Arg Ile Met Cys Arg Arg Gly Phe Glu Met Asp
            420                 425                 430

Phe Ala Glu Leu Leu Leu Glu Asp Tyr Lys Ala Ser Leu Lys Tyr Leu
            435                 440                 445

Ser Asp His Pro Lys Leu Gln Gly Ile Ala Gln Gln Asn Ser Phe Lys
    450                 455                 460

His Thr
465

<210> SEQ ID NO 2
<211> LENGTH: 393
<212> TYPE: PRT
<213> ORGANISM: Homo sapiens

<400> SEQUENCE: 2

Met Lys Thr Ile Thr Leu Tyr Leu Asp Pro Ala Ser Leu Pro Ala Leu
1               5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80

Asn Ile His Leu Asn Ile Ala His Ser Val Gln Leu Ile Arg Pro Ile
                85                  90                  95

Leu Ala Tyr Arg Phe Lys His Leu Asp Arg Val Ser Ile Gln Gln Leu
            100                 105                 110

Asn Leu Tyr Asp Asp Gly Ser Met Glu Tyr Val Asp Leu Glu Lys Glu
        115                 120                 125

Glu Asn Lys Asp Ile Ser Ala Glu Ile Lys Gln Ala Glu Lys Gln Leu
    130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175

Ser Thr Asp Tyr Phe Glu Lys Ala Glu Phe Leu Gln Pro Leu Lys Glu
            180                 185                 190

Tyr Leu Ala Glu Asn Tyr Gln Lys Met Asp Trp Thr Ala Tyr Gln Gln
        195                 200                 205

Leu Thr Pro Glu Gln Gln Ala Phe Tyr Leu Thr Leu Val Gly Phe Asn
```

```
            210                 215                 220
Asp Glu Val Lys Gln Ser Leu Glu Val Gln Gln Ala Lys Phe Ile Phe
225                 230                 235                 240

Thr Gly Thr Thr Thr Trp Gly Asn Thr Asp Val Arg Glu Tyr Tyr
                245                 250                 255

Ala Gln Gln Gln Leu Asn Leu Leu Asn His Phe Thr Gln Ala Glu Gly
                260                 265                 270

Asp Leu Phe Ile Gly Asp His Tyr Lys Ile Tyr Phe Lys Gly His Pro
            275                 280                 285

Arg Gly Gly Glu Ile Asn Asp Tyr Ile Leu Asn Asn Ala Lys Asn Ile
        290                 295                 300

Thr Asn Ile Pro Ala Asn Ile Ser Phe Glu Val Leu Met Met Thr Gly
305                 310                 315                 320

Leu Leu Pro Asp Lys Val Gly Val Ala Ser Ser Leu Tyr Phe Ser
                325                 330                 335

Leu Pro Lys Glu Lys Ile Ser His Ile Ile Phe Thr Ser Asn Lys Gln
                340                 345                 350

Val Lys Ser Lys Glu Asp Ala Leu Asn Asn Pro Tyr Val Lys Val Met
            355                 360                 365

Arg Arg Leu Gly Ile Ile Asp Glu Ser Gln Val Ile Phe Trp Asp Ser
370                 375                 380

Leu Lys Gln Leu Gly Gly Gly Leu Glu
385                 390

<210> SEQ ID NO 3
<211> LENGTH: 34
<212> TYPE: DNA
<213> ORGANISM: Artificial Sequence
<220> FEATURE:
<223> OTHER INFORMATION: primer

<400> SEQUENCE: 3
tcgatcccgc gaaattaata cgactcacta tagg                           34

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
aaagataaat ttagcttgtt gcacttc                                   27

<210> SEQ ID NO 5
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(29)
<223> OTHER INFORMATION: n is a, c, g, or t

<400> SEQUENCE: 5
gaagtgcaac aagctaaatt tatctttnns ggcacg                         36

<210> SEQ ID NO 6
<211> LENGTH: 24
<212> TYPE: DNA
```

```
<213> ORGANISM: Artificial Sequence
<220> FEATURE:
<223> OTHER INFORMATION: primer

<400> SEQUENCE: 6
aggatgccct ttaaagtaga tttt                                          24

<210> SEQ ID NO 7
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g, or t

<400> SEQUENCE: 7
aaaatctact ttaaagggca tcctnnsggt ggtgaaatta atgactacat tctga         55

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
tgaacttgca acaccaccca c                                             21

<210> SEQ ID NO 9
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t

<400> SEQUENCE: 9
gtgggtggtg ttgcaagttc annstatttc                                    30

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
caaaaaaccc ctcaagaccc gttta                                         25
```

METHOD FOR CELL-FREE PROTEIN SYNTHESIS INVOLVED WITH PH CONTROL WITH AMINO ACID DECARBOXYLASE

CROSS REFERENCE TO RELATED APPLICATIONS

The present application is a continuation in part application to International Application No. PCT/KR2015/005910, with an International Filing Date of Jun. 12, 2015, which claims the benefit of Korean Patent Application No. 10-2014-0071736, filed in the Korean Intellectual Property Office on Jun. 12, 2014, the entire contents of which are incorporated herein by reference.

BACKGROUND

1. Technical Field

The present invention relates to a method for cell-free protein synthesis in which pH is controlled by using an enzyme. More specifically, the present invention relates to a method for cell-free protein synthesis which can provide, by controlling a decrease in pH using an amino acid decarboxylase, a cell-free protein in an enhanced synthesis amount, and can be used for screening of an active type protein without separating or purifying a synthesized protein.

2. Background Art

The cell-free protein synthesis generally indicates a technique for producing a large amount of a target protein within a short period of time in which only the intracellular protein synthesis mechanism involved with cellular protein synthesis and the factors of the mechanism are selected and only the protein synthesis process is artificially repeated outside a cell while the physiological regulation mechanism of a cell is excluded. With regard to the components required for biosynthesis of a protein, i.e., ribosome, initiation factor, elongation factor, termination factor, aminoacyl tRNA synthase, or the like, those included in a cell lysate can be used, or they can be separately added and used (Yoshihiro Shimizu et. al, 2001, Nature Biotechnology, 19(8): 751-755; Tae-Wan Kim et. al, 2006, Journal of Biotechnology, 126(4): 554-561).

Because continuous supply of ATP is required for a transcription reaction and a translation reaction of DNA by the components for protein synthesis, it is necessary for a solution for cell-free protein synthesis to have a mechanism for ATP regeneration. In this regard, it is noted that materials like acetyl phosphate, creatine phosphate, or phosphoenol pyruvate (PEP) that are conventionally used for ATP regeneration have a problem that they have not only poor ATP regeneration efficiency but also poor protein synthesis efficiency due to accumulation of inorganic phosphate.

To solve such problem, it is recently reported by Swartz, et. al. that, by using glucose as a material for ATP regeneration required for cell-free protein synthesis, smooth supply of ATP for a long period of time can be achieved, thus making it possible to have cell-free protein synthesis with high productivity, and it was also shown that, by using an inexpensive energy source like glucose for ATP regeneration, the productivity and economic efficiency of cell-free protein synthesis can be significantly enhanced (Kara A. Calhoun et. al, 2005, Biotechnology Progress, 21(4):1146-1153). As it undergoes a catabolic reaction and an oxidative phosphorylation process that are caused by enzymes present in a cell extract, glucose can regenerate several ATP molecules. Accordingly, it can be used as an efficient energy source in a system for cell-free protein synthesis.

However, when glucose and intermediates of glycolysis other than glucose are used for the reaction of cell-free protein synthesis, a decrease in pH of the reaction solution is caused in accordance with accumulation of organic acids that are derived from the glucose and intermediates. Such decrease in pH becomes a factor for limiting the productivity of cell-free protein synthesis as the activity of protein synthesis mechanism is inhibited by pH decrease (Ho-Cheol Kim et. al., 2011, Process Biochemistry, 46(6): 1366-1369). As such, it is essential to control the pH to be in a range in which the components of protein synthesis mechanism in a cell extract are not affected by it.

To have pH control, use of a chemical pH buffer agent like Tris and HEPES is generally carried out. However, pH decrease in a reaction solution caused by use of glucose or the like is not sufficiently inhibited by a pH buffer agent at the concentration which is generally used at present moment, and there is also a problem that, because the use of a buffer agent at high concentration is accompanied with a corresponding increase in salt concentration, it may become a factor which can inhibit the protein synthesis.

Furthermore, because the buffer solution used for pH control cannot be removed after the reaction of cell-free protein synthesis, if the activity of an enzyme synthesized by cell-free protein synthesis is to be analyzed in view of pH, a change in pH caused by the enzyme activity is suppressed due to the inclusion of the buffer solution of a solution for synthesis in a solution for activity analysis, and thus an accurate analysis of enzyme activity cannot be made.

Meanwhile, in Korean Patent Registration No. 0749053, a method for cell-free protein synthesis is disclosed, and in Korean Patent Registration No. 0733712, production of a cell extract for cell-free protein synthesis and a method for protein synthesis using it are disclosed. Furthermore, in Korean Patent Registration No. 1229849, a method for enhancing protein expression yield of cell-free protein synthesis according to addition of an anti-foaming agent is disclosed. However, a technique for solving the aforementioned problems has not been suggested.

SUMMARY

An embodiment of the present invention is devised in view of the circumstances described above, and as it is confirmed that the efficient cell-free protein synthesis can be achieved by pH control using a mutant amino acid decarboxylase during a process of cell-free protein synthesis, an embodiment of the present invention is completed accordingly.

To achieve one or more of the aforementioned aspects, an embodiment of the present invention provides a method for cell-free protein synthesis which is characterized in that pH is controlled by adding an enzyme to a reaction solution for cell-free protein synthesis.

An embodiment of the present invention further provides a library of proteins that are synthesized by the above method for cell-free protein synthesis.

An embodiment of the present invention still further provides a method for screening an active type protein by using a library of proteins that are synthesized by the above method for cell-free protein synthesis.

The present invention relates to a method for cell-free protein synthesis which is characterized in that pH is controlled by using an enzyme. When cell-free protein synthesis is carried out by using glutamic acid decarboxylase (GAD)

and glutamic acid, glutamic acid is consumed and depleted in accordance with a progress of the cell-free protein synthesis reaction. Thus, the reaction solution for cell-free protein synthesis obtained after an enzymatic synthetic reaction is in a buffer-free state in which the pH buffering activity is absent. As such, if a part of the reaction solution for cell-free protein synthesis is collected and the activity of an enzyme included in the reaction solution for cell-free protein synthesis is analyzed, highly-sensitive enzyme activity analysis can be achieved as there is no factor suppressing the pH change.

Furthermore, when a chemical buffer solution is used, the pH decrease is not sufficiently suppressed and also, as the use of a buffer agent at high concentration is accompanied with a corresponding salt concentration increase, the amount of protein synthesis remains at a low level due to the salt concentration increase which serves as a factor for suppressing the protein synthesis. On the other hand, when the GAD system of an embodiment of the present invention is used, the effect of suppressing the pH decrease is excellent so that it is possible to have an effect of enhancing the protein synthesis amount.

BRIEF DESCRIPTION OF THE DRAWING

FIG. 2 is a graph illustrating the average expression amount of sialyl transferase (ST) which has been obtained by cell-free protein synthesis at condition of 240 mM buffer solution (HEPES buffer).

DETAILED DESCRIPTION

Figure 1A:
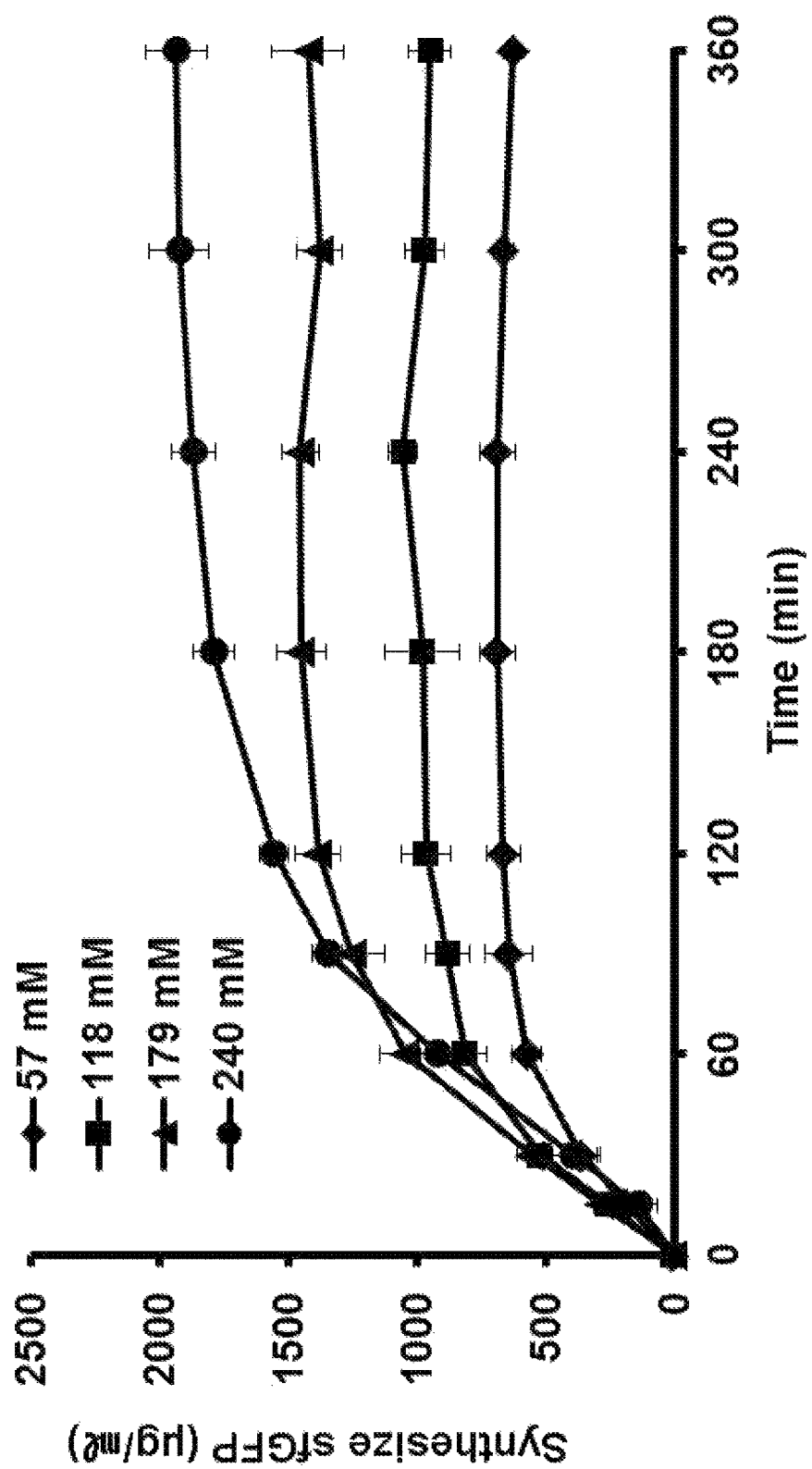
FIGS. 1A and 1B graphs for determining the concentration of synthesized sfGFP (μg/ml) (FIG. 1A) and degree of pH decrease depending on the concentration of a chemical buffer solution (HEPES buffer) (FIG. 1B) (—♦— 57 mM, —■— 118 mM, —▲— 179 mM, and —●— 240 mM) in cell-free protein synthesis.

To achieve one or more of the aspects of the present invention in relation to the method for cell-free protein synthesis, an embodiment of the present invention provides a method for cell-free protein synthesis which is characterized in that pH is controlled by adding an enzyme to a reaction solution for cell-free protein synthesis.

The reaction solution for cell-free protein synthesis comprises a cell extract, a gene, an energy source, a buffer solution, an amino acid, or the like, and by further comprising an amino acid such as glutamic acid, arginine, or lysine, it is possible to use those amine acids as an enzyme substrate.

The aforementioned enzyme indicates an amino acid decarboxylase, which is a hydrolyzing enzyme to produce amines by acting on various amino acids and removing a C—C bond to generate carbon dioxide and amines which correspond to each amino acid.

Preferred examples of the amino acid decarboxylase include at least one selected from glutamate decarboxylase EC 4.1.1.15, arginine decarboxylase EC 4.1.1.19, lysine decarboxylase EC 4.1.1.18, aspartate 4-decarboxylse EC 4.1.1.12, valine decarboxylase EC 4.1.1.14, histidine decarboxylase EC 4.1.1.22, tyrosine decarboxylase EC 4.1.1.25, aromatic-L-amino acid decarboxylase EC 4.1.1.28 acting on phenyl alanine, tryptophane, tyrosine or the like, phenylalanine decarboxylase EC 4.1.1.53, and methionine decarboxylase EC 4.1.1.57. More preferably, it is at least one selected from glutamate decarboxylase EC 4.1.1.15, arginine decarboxylase EC 4.1.1.19, and lysine decarboxylase EC 4.1.1.18. Even more preferably, it is glutamic acid decarboxylase having an amino acid sequence of SEQ ID NO: 1 of which the glutamic acid at the $89^{th}$ position is substituted with glutamine and the amino acids at the $465^{th}$ position and the $466^{th}$ position are deleted, but not limited thereto. It is possible that part of the amino acids of the amino acid decarboxylase may be deleted, substituted, or inserted, and amino acids in modified form like phosphorylation or methylation form may be also included.

As for the aforementioned pH, it is preferable that the pH is not decreased to 6.5 or lower. It is more preferable that the pH is controlled to 6.5 or 8.0.

The aforementioned amino acid decarboxylase can control pH by removing the hydrogen ions that are produced during regeneration of ATP from a carbon source. It is preferable that the carbon source is at least one selected from monosaccharides, disaccharides, polysaccharides, polyhydric alcohols, and organic acids. More preferably, it is glucose, but not limited thereto.

Also, the method for controlling pH using enzyme is not limited to cell-free protein synthesis. It may also be used for controlling pH during enzymatic reactions inside or outside cells.

Also provided by the present invention is a library of proteins that are synthesized by the above method for cell-free protein synthesis. The library of proteins is preferably a library of sialyl transferase proteins, but not limited thereto. The sialyl transferase is an enzyme which plays a role of attaching sialic acid to a terminal of a sugar chain of a glycoprotein, and sialyl lactose and sialyl oligosaccharides derived from the enzyme are characterized in that they can be also a major source for supplying sialic acid to a body tissue, a skin, a brain, or the like.

Still also provided by the present invention is a method for screening an active type protein which is characterized in that an active type protein is screened by having, as a subject, a library of proteins that are synthesized by the method for cell-free protein synthesis of an embodiment of the present invention. The protein library is characterized in that it allows screening without having any separation or purification of proteins.

Herein below, the present invention is explained in greater detail in view of the Examples. However, it would be evident for a person having common knowledge in the pertinent art that the following Examples are given only for specific exemplification of the present invention and by no means the scope of the present invention is limited to those examples.

EXAMPLES

[Materials and Experimental Methods]
1. Preparation of Cell Extract (S12 Extract)

5 ml of BL21-Star (DE3) derived from *E. coli* was inoculated to a LB medium and incubated for 12 hours at 37° C. After that, it was subjected to overnight subculture at 37° C. in 40 ml of 2×YTPG medium, and then inoculated to a fermentation tank containing 4 L of 2×YTPG followed by culture at the same temperature. When the absorbance ($OD_{600}$) becomes 0.6, 1 mM isopropylthio-β-D-galactoside (IPTG) was finally added to the fermentation tank to express T7 RNA polymerase. The cell culture was terminated when the absorbance ($OD_{600}$) becomes 4.5, and according to centrifuge (4,500 rpm, 15 minutes, 4° C.), only the *E. coli* cell pellets were collected from the medium.

The collected *E. coli* cells were subjected 3 times to a process of thorough washing of the cells by adding 20 mM buffer solution A [10 mM Tris-acetate buffer (pH 8.2), 14 mM magnesium acetate, 60 mM potassium glutamate, 1 mM dithiothreitol (DTT), 0.05% (v/v) 2-mercaptoethanol (2-ME)] per gram of the cells.

12.7 ml of the buffer solution B (buffer solution A from which 2-ME is removed) was added per 10 grams of the *E. coli* cells which have been washed as described above. After dispersing them homogeneously, the cells were disrupted using a press (French Pressure Cell Press, Thermo Scientific) at constant pressure (12,000 psi). The cell lysate was subjected to centrifuge (30,000 rcf, 30 minutes, 4° C.) to obtain a supernatant, which was then incubated at 37° C. for 30 minutes. After aliquoting the supernatant in a small amount, it was stored in an ultra-low temperature freezer (−80° C.) until use.

2. Cell-Free Protein Synthesis and Determination

The cell-free protein synthesis reaction was carried out according to addition to a small tube of 1.75 ml and reaction in an incubator at 30° C.

57 mM Buffer solution (HEPES-KOH, pH 8.2), 1.4 mM ATP, 1.0 mM each of CTP, GTP, and UTP, 1.8 mM DTT, 90 mM potassium glutamate, 80 mM ammonium acetate, 8 mM magnesium acetate, 20 mM potassium phosphate, 34 μg/mL 1-5-formyl-5,6,7,8-tetrahydrofolic acid (folinic acid), 3.2 mM each of 20 amino acids, 2% polyethylene glycol (PEG) 8000, 80 mM D-glucose, 13.3 μg/mL plasmid, and 27% (v/v) S12 extract were used for the reaction solution for cell-free protein synthesis.

Concentration of the above buffer solution (HEPES-KOH, pH 8.2), amino acids, glucose, and L-glutamate was adjusted as necessary. Total amount of the produced proteins was determined based on the radioactivity of a radioisotope after TCA-precipitation.

Quantification of active type sfGFP was performed by measuring the fluorescence intensity using VICTOR X3 multilabel plate reader (Perkin-Elmer, Waltham, Mass.). Size of the produced sfGFP was determined based on Coomassie blue-stained Tricine-SDS-PAGE gels.

The change in pH was recorded by measuring the pH every hour using 90 μl of a reaction solution and a micro pH electrode (i.e., micro-combination pH-electrode; InLab 423, Mettler-Toledo GmbH, Switzerland).

3. Cell-Free Protein Synthesis using Glutamic Acid Decarboxylase (GAD) and Purification Each gene sequence of the wild type GAD enzyme and the mutant GAD (Glu89Gln/Δ465-466) was cloned in the pET28b vector, and used for transformation of *E. coli* BL21 (DE3). Each bacterial cell was cultured at a temperature of 37° C. in 500 ml LB medium in which kanamycin is included. For the expression of GAD, 1 mM IPTG was added when $OD_{600}$ value reaches 2.5. After further culturing the cells for 2 hours at the same conditions, the cells were collected and washed with the buffer solution A. The cell aggregate was then disintegrated by using the buffer solution B, and disrupted at a pressure of 12,000 psi by using a press (French Pressure Cell Press). According to centrifuge at 30,000 rcf and 4° C. for 30 minutes, a supernatant was collected.

The collected supernatant was separated and purified by using Ni-NTA agarose beads (Qiagen), and then concentrated with the buffer solution B by using VIVA-spin 20 (MWCO 10 kDa, Sartorius). Thereafter, the protein concentration was measured by Bradford method, and the concentrate was stored at −80° C. until use.

Example 1. Determination of Amount of Synthesized Protein and Change in pH Depending on Concentration of Buffer Solution of Cell-Free Protein Synthesis To determine a pH change depending on the concentration of a buffer solution of cell-free protein synthesis, cell-free protein synthesis of sfGFP protein was carried out by using a buffer solution of 57 mM, 118 mM, 179 mM, or 240 mM.

Figure 1B:
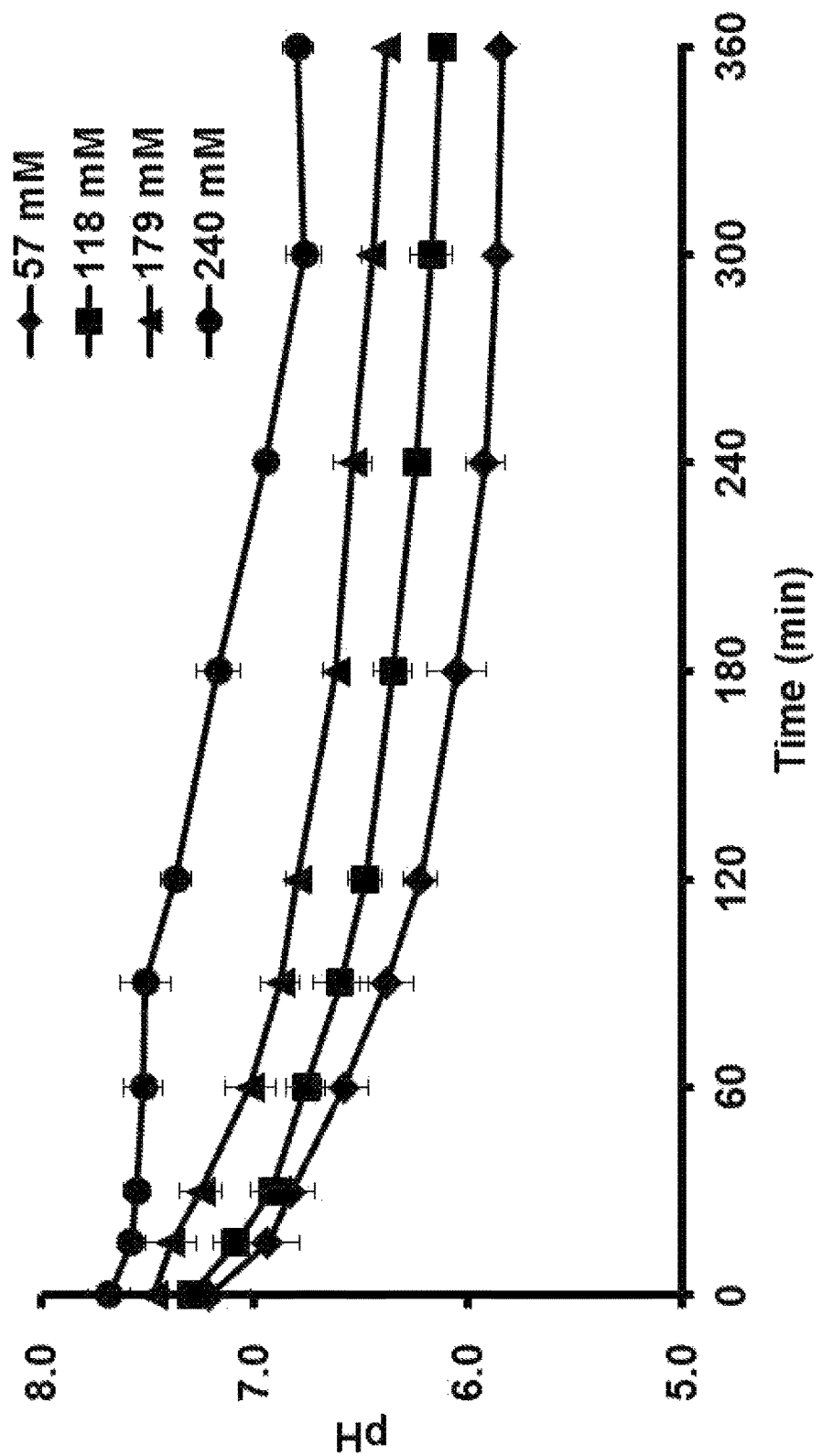

As shown in FIGS. 1A and 1B, it was found that the decrease amount of pH is reduced and the protein synthesis amount is increased as the concentration of the chemical buffer solution (I.e., HEPES buffer) is increased. At that time, in order to maintain the pH level of 6.5 which is the minimum condition required for the reaction using an excess amount of glucose (80 mM), concentration of the buffer solution (I.e., HEPES buffer) was optimized, i.e., 240 mM or less. As a result of carrying out the cell-free protein synthesis at a condition including 240 mM buffer solution, it was confirmed that sfGFP protein is obtained at a level of 2 mg/ml, approximately.

After that, for screening the activity of a sialyl transferase, by using 96 sialyl transferase gene libraries, cell-free protein synthesis was carried out at a condition including 240 mM buffer solution which has been optimized as described above.

As shown in FIG. 2, when a library of 96 types of sialyl transferase is used for cell-free protein synthesis in a 96-well plate, it was found that the sialyl transferase is expressed at a level of 630±101 μg/ml. However, according to the reaction for measuring the activity in which a pH indicator and a substrate are used, no color change was observed. It is believed that no color change of a pH indicator was based on the buffer activity of the buffer solution at high concentration (i.e., HEPES buffer, 240 mM) against the change in hydrogen ion concentration which occurred even in a solution for measuring the activity.

As such, after separating and purifying the sialyl transferase, it was determined whether or not the activity analysis can be made with the enzyme. As a result, in case of the separated and purified enzyme, color change was observed depending on the activity of the protein.

It was confirmed based on Example 1 that, for cell-free protein synthesis, a buffer mechanism exhibiting no interference in activity analysis is required under pH control.

Example 2. Determination of Effect of Controlling pH Change by Glutamic Acid Decarboxylase in Cell-Free Protein Synthesis and Expression Amount of sfGFP Protein As a buffer mechanism which exhibits no interference in activity analysis under pH control of cell-free protein synthesis, an amino acid decarboxylase was used.

Numerous microorganisms have an intrinsic buffer system for their survival at acidic conditions. For example, in case of *E. coli*, several kinds of an amino acid decarboxylase (i.e., arginine decarboxylase, glutamic acid decarboxylase, and lysine decarboxylase) are induced and expressed at acidic conditions. Those enzymes are known to remove hydrogen ions while dissociating the carboxyl group from each amino acid and have a function of maintaining intracellular pH of *E. coli* even at acidic conditions. By taking advantage of such characteristics, the anti-acidic mechanism of those microorganisms was applied to control the pH change in a cell-free protein synthesis system.

In this Example 2, to remove the hydrogen ions that are generated according to a glycolysis process in a cell extract, glutamic acid decarboxylase (GAD) was used. One molecule of glutamic acid plays the role of removing the same mole number of hydrogen ions while the acid is converted into one molecule of derivatized amino acid (γ-aminobutyric acid) by the above enzyme. As such, when GAD and glutamic acid are added to a solution for cell-free protein synthesis, the hydrogen ions that are generated during the ATP regeneration process are removed so that the pH can be stably maintained.

However, the system for controlling pH by using GAD shows disappearance of the buffer effect as soon as the glutamic acid is depleted. Furthermore, as the wild type GAD activity of pH-dependent *E. coli* exhibits the enzyme activity and protein cooperativity at pH of from 3.8 to 4.6, the GAD activity is not shown at pH of from 6.5 to 8.0, which is the optimum pH of a cell-free protein synthesis system.

Recently however, it is luckily known that the pH dependency of the GAD derived from *E. coli* is decided by several specific amino acid residues. Namely, it is noted that the pH dependency of the GAD enzyme can be modified based on engineering of the enzyme. As an example, according to the studies carried out by Ho, et. al., it was shown that, when glutamic acid as the $89^{th}$ amino acid of *E. coli* GAD is substituted with glutamine, the activity can be exhibited even at a pH in a neutral range. Furthermore, when the pH dependent cooperativity is removed by deleting the histidine and threonine, which are the $465^{th}$ and the $466^{th}$ amino acid, respectively, it was shown that the pH range in which the activity is shown can be broadened while the pH dependent cooperativity is removed. According to application of this effect based on mutation, it was able to obtain a mutant GAD (Glu89Gln/Δ465-466) which exhibits the activity at a pH close to neutral pH and also in a wide pH range.

For the pH control by an enzyme, the inventors of the present invention decided to use the mutant GAD (Glu89Gln/Δ465-466) as described above, and it was expected that the pH decrease is reduced in a cell-free protein synthesis reaction in which glucose is used.

Accordingly, in this Example 2, the effect of controlling the pH change by glutamic acid decarboxylase (GAD) in cell-free protein synthesis and the expression amount of sfGFP protein were determined.

Figure 3A:
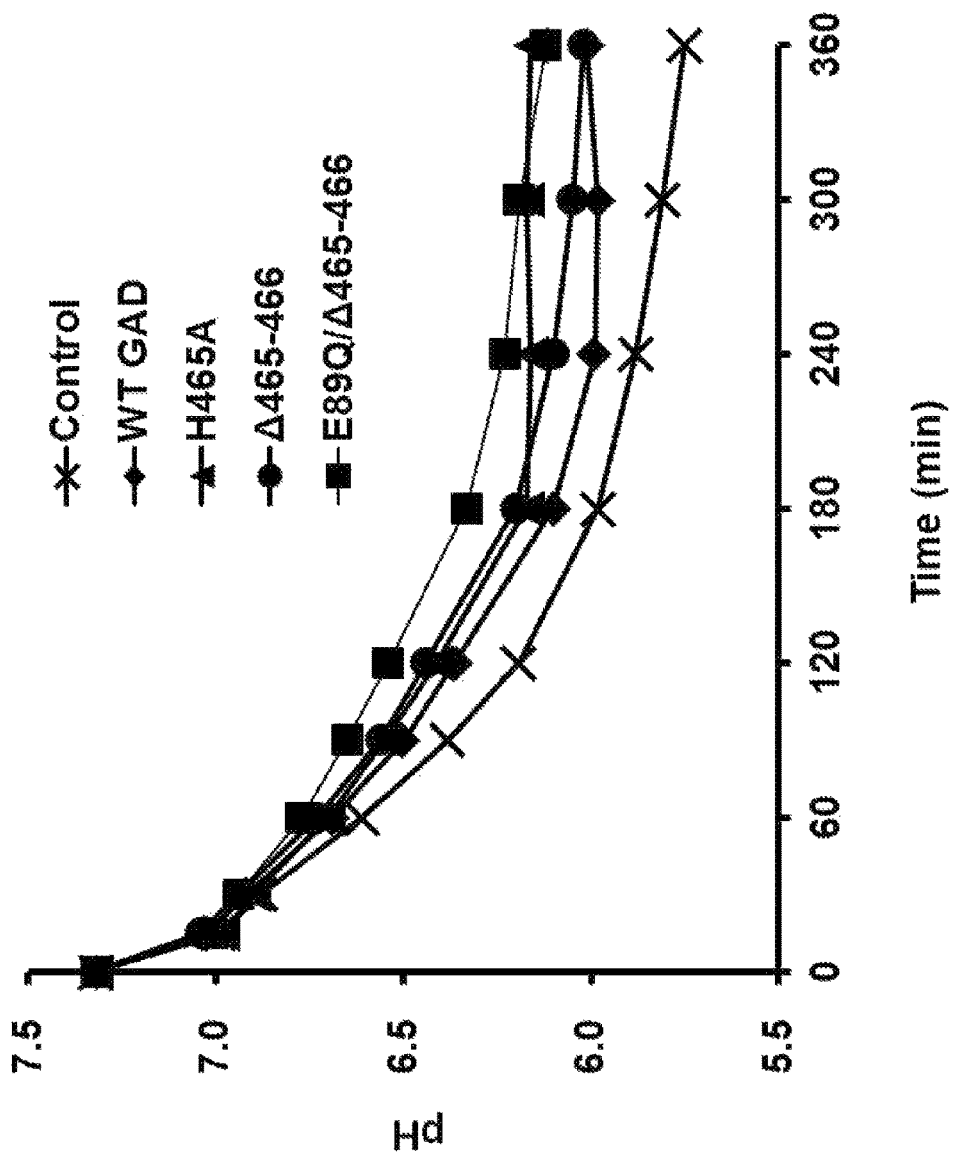
FIGS. 3A and 3B are graphs for determining the effect of controlling pH by glutamic acid decarboxylase (FIG. 3A) and the expression amount of sfGFP protein at each condition when the cell-free protein synthesis has been performed at condition of 57 mM buffer solution (HEPES buffer) (FIG. 3B). —×— Control is a control group in which glutamic acid decarboxylase is not added; —▲— H465A represents addition of mutant glutamic acid decarboxylase of which histidine at the $465^{th}$ position is substituted with alanine; —●— Δ465-466 represents addition of mutant glutamic acid decarboxylase of which histidine at the $465^{th}$ position and threonine at the $466^{th}$ position are deleted; and —■— Glu89Gln/Δ465-466 represents addition of mutant glutamic acid decarboxylase of which glutamic acid at the $89^{th}$ position is substituted with glutamine and histidine at the $465^{th}$ position and threonine at the $466^{th}$ position are deleted.

According to the result, it was found that the amount of the protein obtained by a cell-free protein synthesis reaction is significantly increased while the time during which neutral pH is maintained has also increased. In a case in which 57 mM HEPES-KOH buffer solution is used as a control group, pH of the reaction solution decreases to 6.5 or less within 80 minutes. However, when the GAD protein at 0.4 mg/ml is added to the same reaction solution, the time till to have pH of 6.5 has increased to about 130 minutes (FIG. 3A).

Figure 3B:
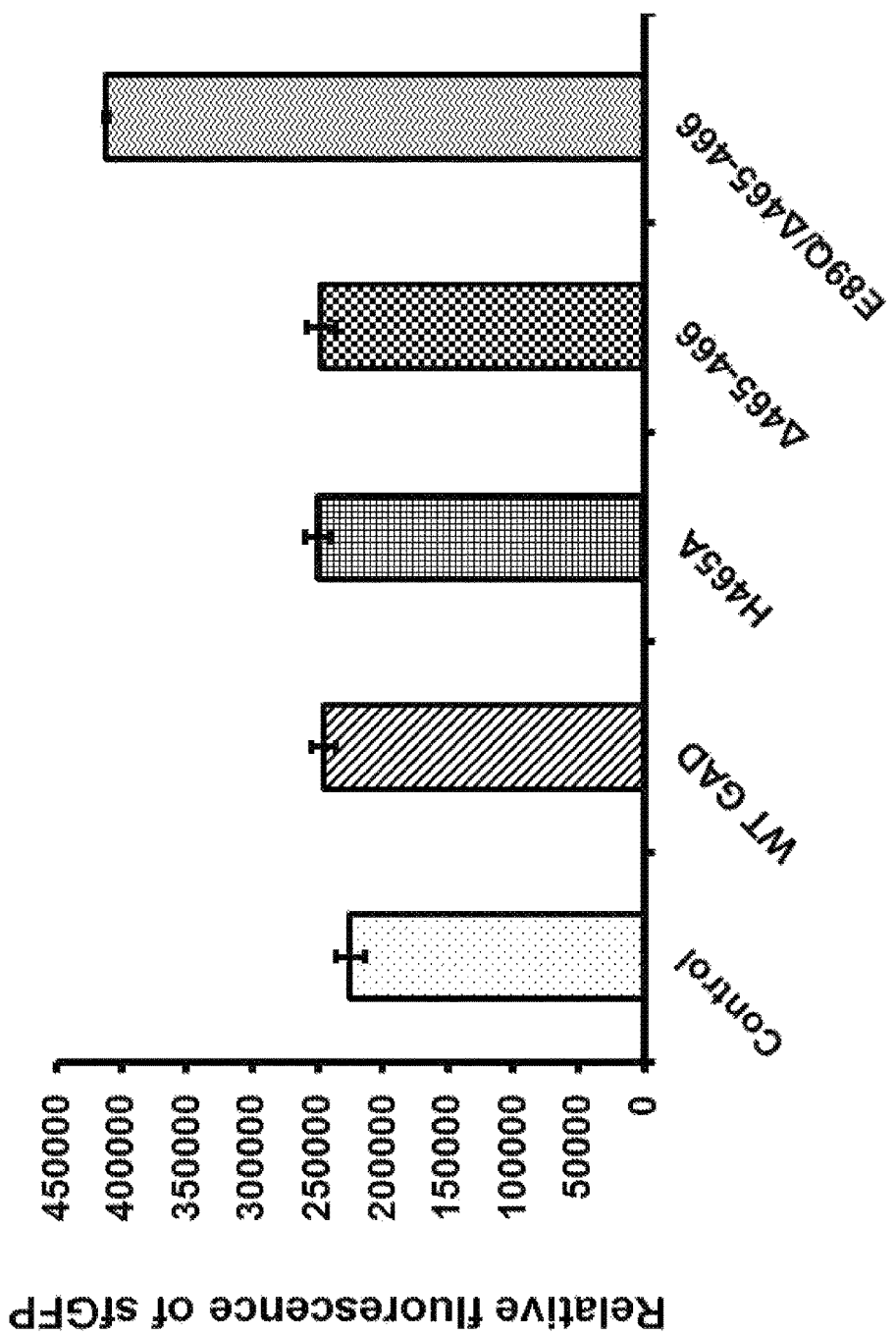

As shown in the above, according to the reaction in which the pH decrease rate is lowered, the amount of the synthesized protein has increased simultaneously, showing the productivity of about 2 times or so. On the other hand, in case of adding the wild type GAD, the effect of controlling pH was hardly shown, and the protein productivity was almost the same as the reaction of a related art (FIG. 3B). Such result indicates that, in terms of the pH decrease of a reaction solution, the mutant GAD (Glu89Gln/Δ465-466) is more effective than the wild type GAD.

Figure 4:
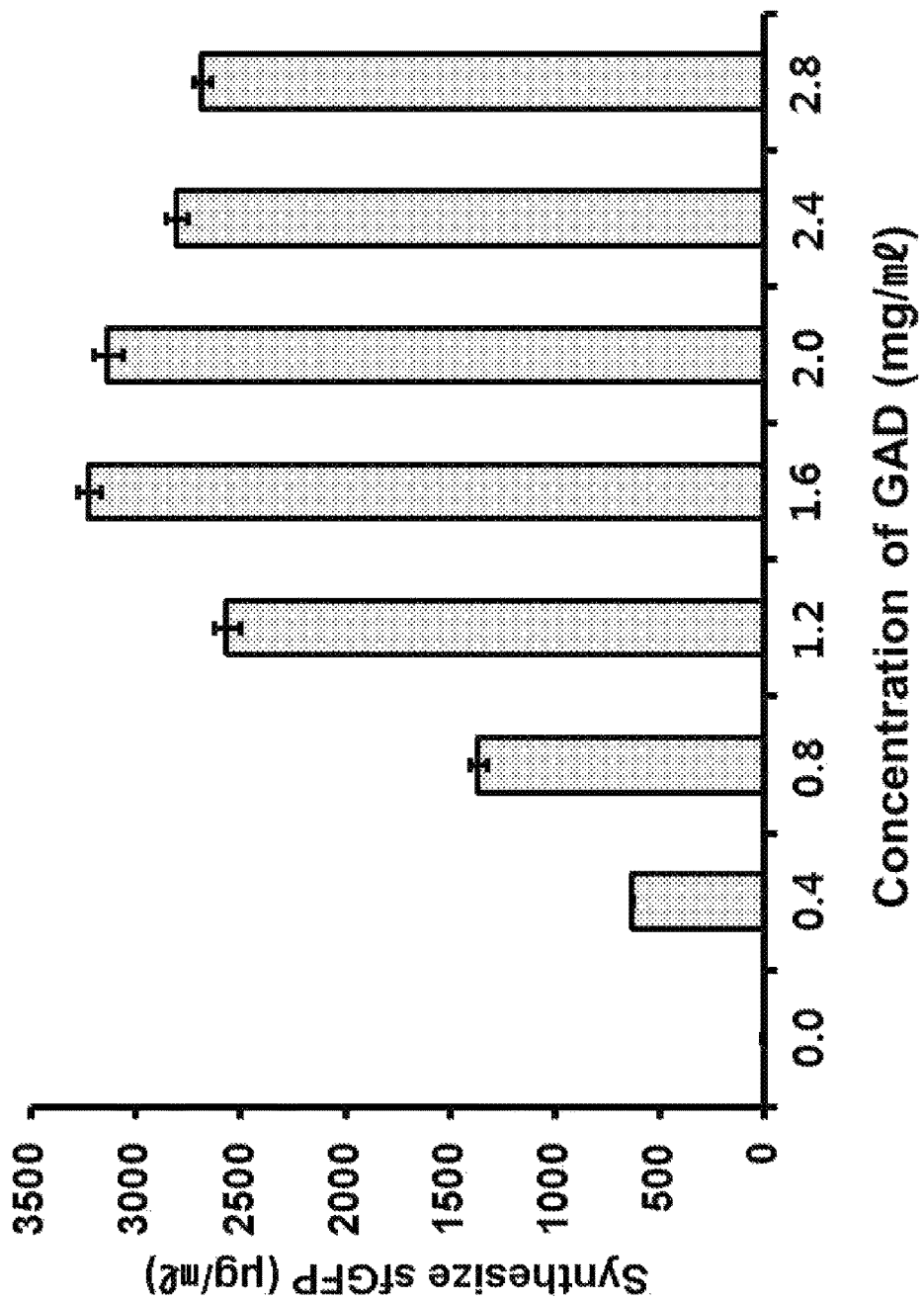
FIG. 4 is a graph illustrating the expression amount of sfGFP protein depending on the concentration of a mutant glutamic acid decarboxylase of which glutamic acid at the $89^{th}$ position is substituted with glutamine and histidine at the $465^{th}$ position and threonine at the $466^{th}$ position are deleted

Furthermore, when the concentration of GAD (Glu89Gln/Δ465-466) in a reaction solution for cell-free protein synthesis is increased to 1.6 mg/ml or more, even higher anti-oxidizing activity is obtained so that the effect of having higher protein productivity in a reaction solution for cell-free protein synthesis was shown (FIG. 4).

Figure 5:
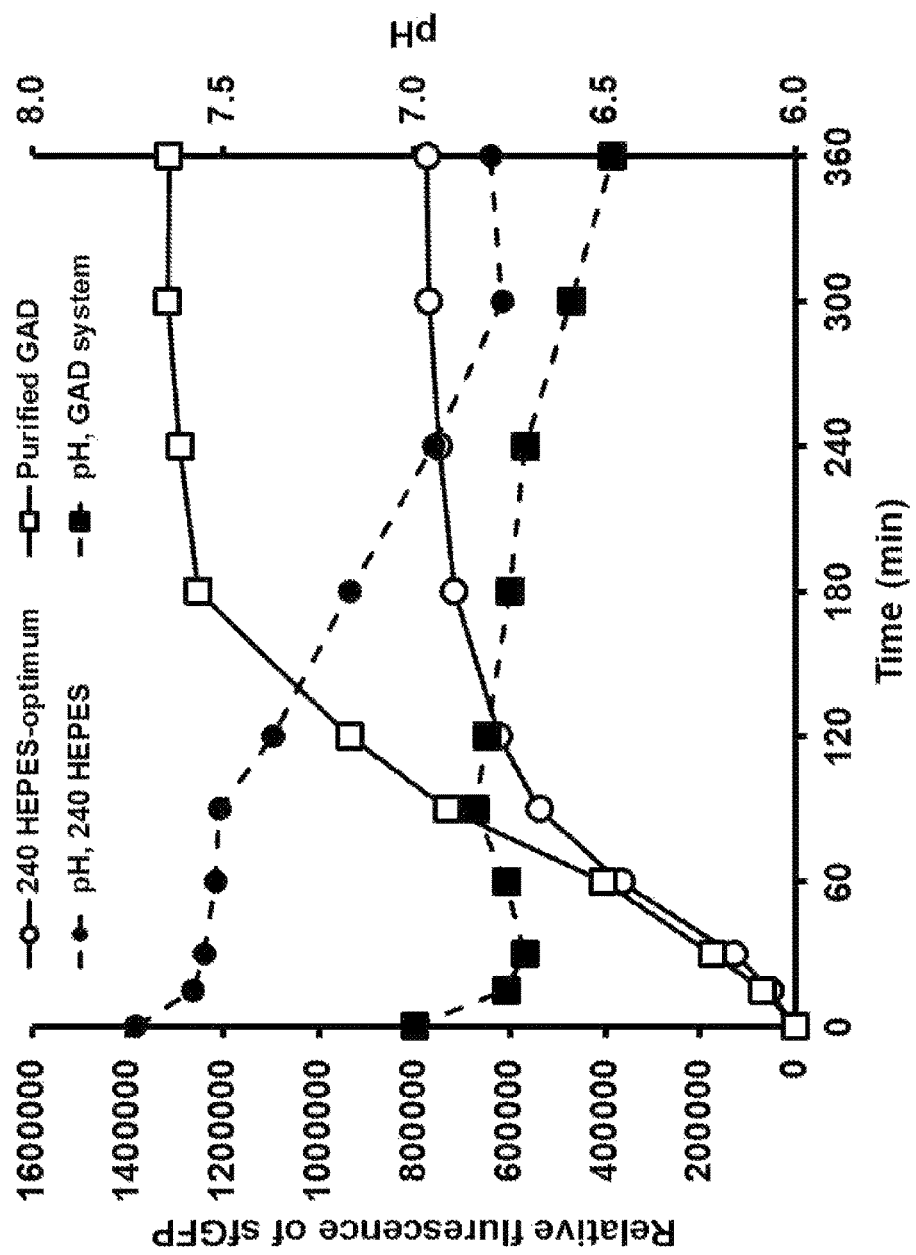
FIG. 5 is a graph for comparing the change in pH and protein expression amount over time in cell-free protein synthesis in which 1.6 mg/ml GAD (Glu89Gln/Δ465-466) and 240 mM buffer solution (HEPES-KOH) are used.

Furthermore, the pH change and the amount of synthesized protein over time were compared when each of 1.6 mg/ml GAD (Glu89Gln/Δ465-466) and 240 mM HEPES-KOH is used for the reaction solution for cell-free protein synthesis. As a result, it was found as shown in FIG. 5 that, even if the HEPES-KOH as a buffer solution is completely removed from the reaction solution, the pH can be fully maintained if GAD is present at constant concentration or higher.

Figure 6:
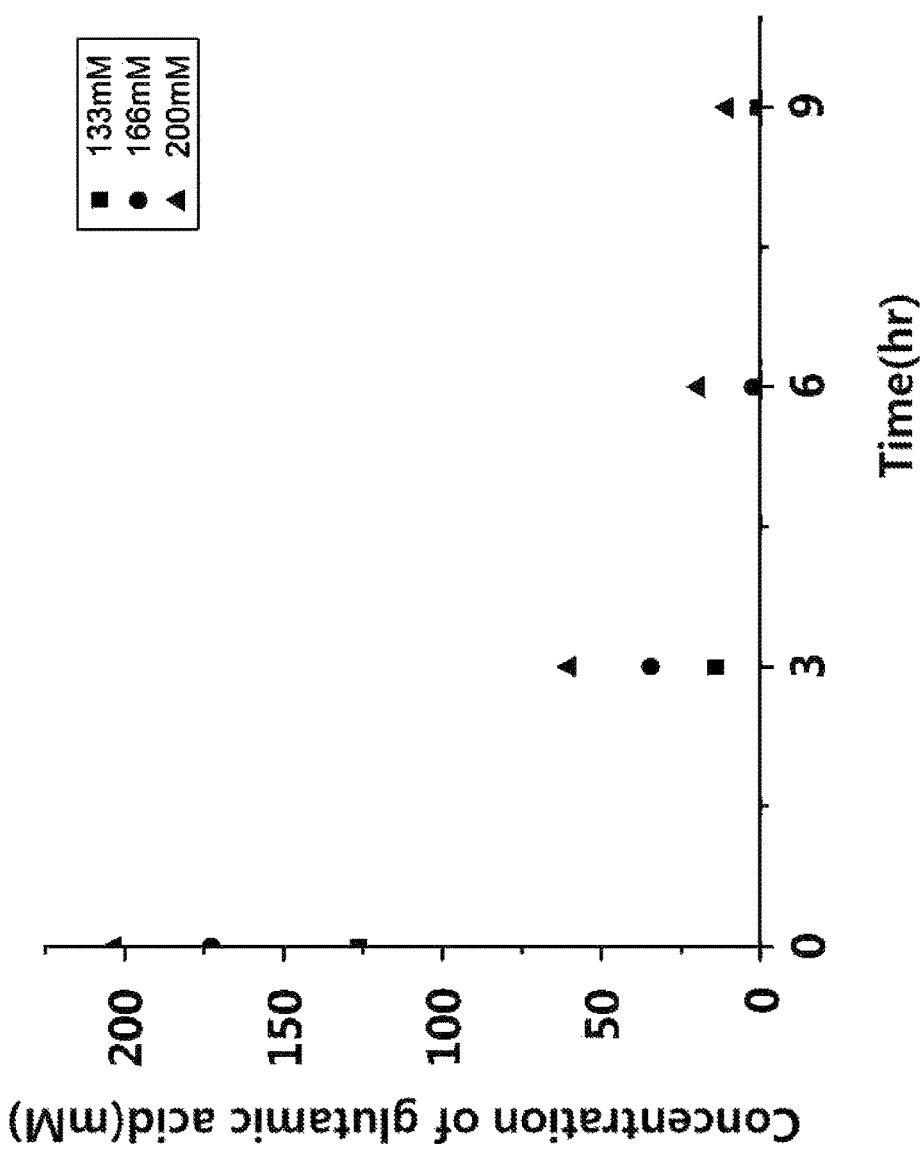
FIG. 6 is a graph for determining the time for glutamic acid depletion at each initial concentration of glutamic acid, in which the depletion is caused by cell-free protein synthesis.

Furthermore, as the initial concentration (166 mM) of glutamic acid included in the reaction solution completely disappears according to the reaction for 6 hours, a buffer-free condition is yielded (FIG. 6). Thus, it was found that the time for cell-free protein synthesis is preferably as long as 6 hours if glutamic acid is used at initial concentration of 166 mM. In this regard, further addition of glutamic acid after 6 hours to have a progress of the reaction is not excluded, and it is expected that the time for cell-free protein synthesis reaction can be extended by suitably regulating the glutamic acid concentration.

Figure 7:
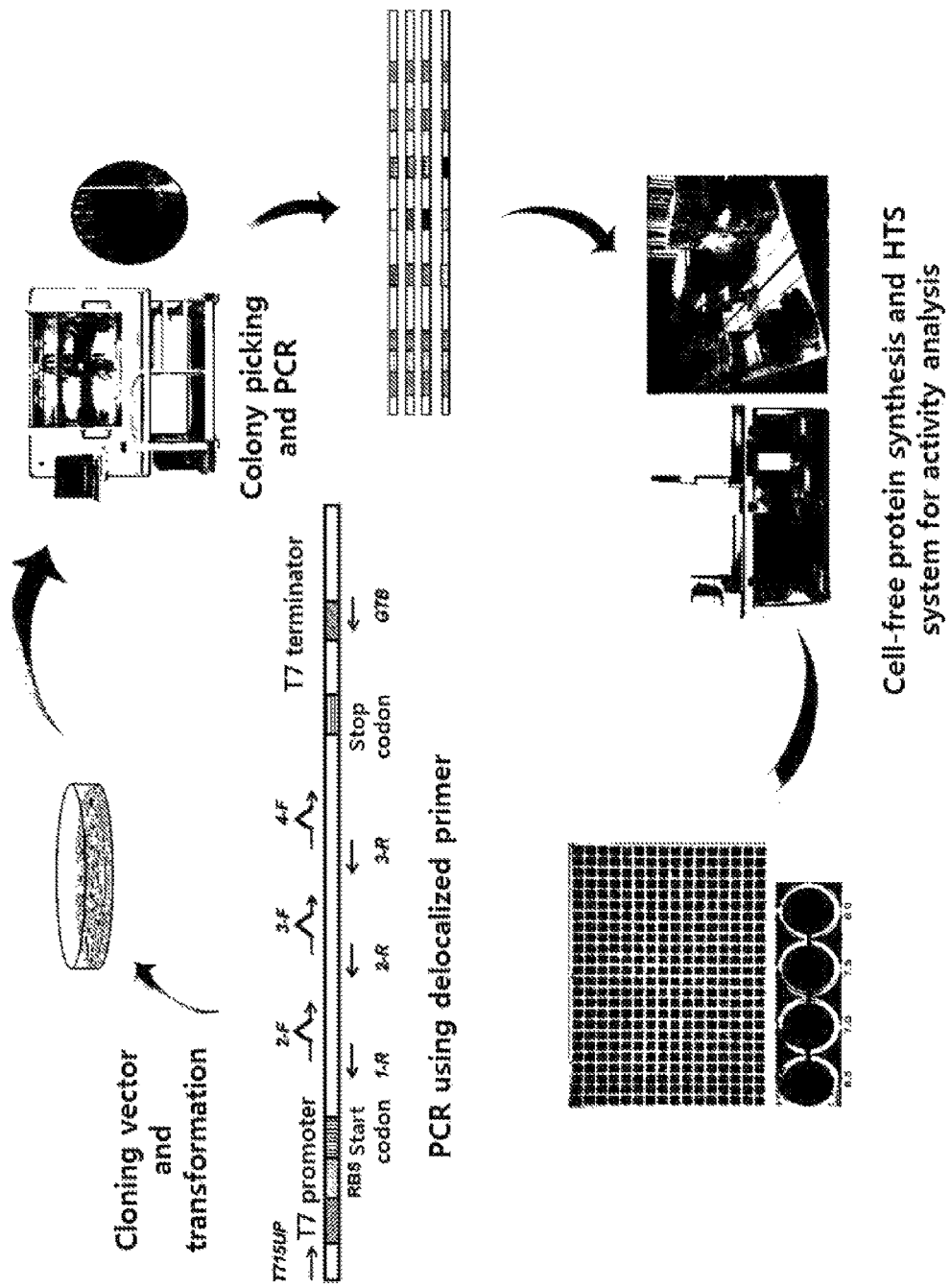
FIG. 7 is a drawing illustrating the assay process including establishment of the library of an embodiment of the present invention, cell-free protein synthesis using an amino acid decarboxylase, and analysis of the synthesized enzyme.

Example 3. Establishment, Expression, and Activity Analysis of Sialyl Transferase Library In this Example 3, establishment of a sialyl transferase library, cell-free protein synthesis using an amino acid decarboxylase, and an assay for analyzing the activity of synthesized enzyme were performed according to the process shown in FIG. 7.

Figure 8:
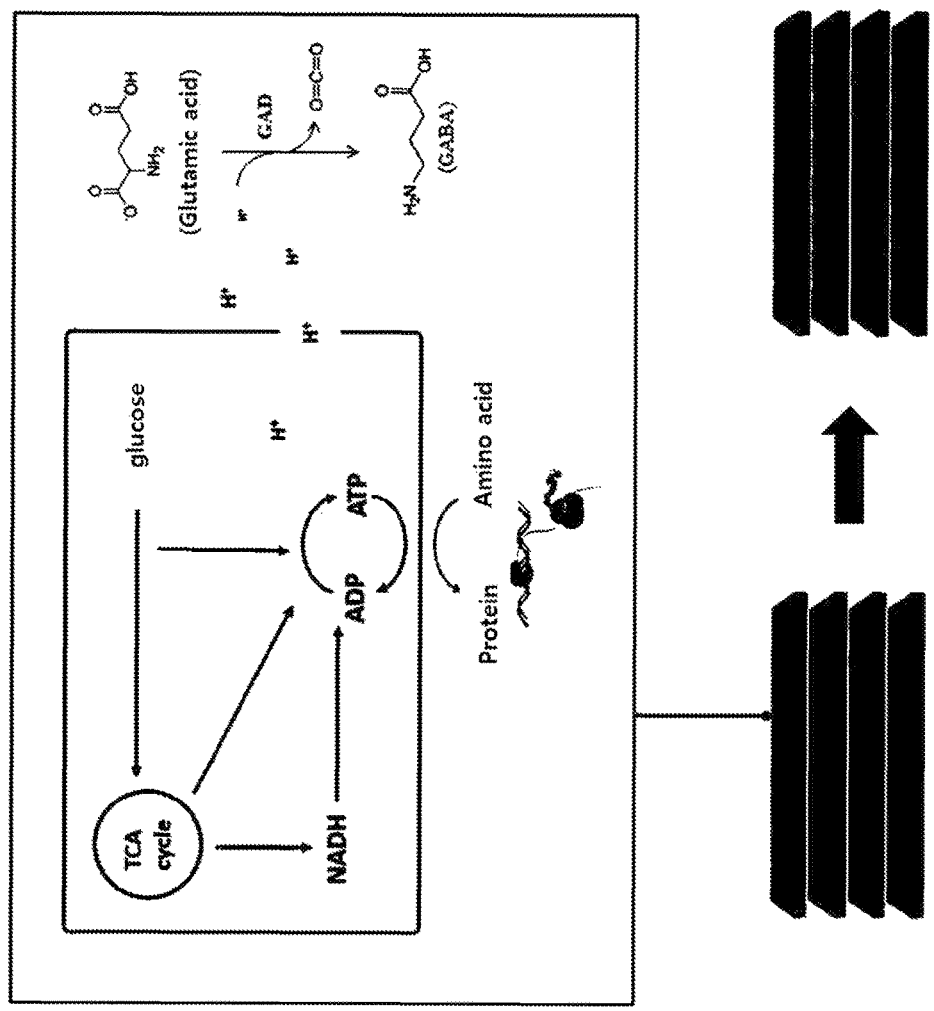
FIG. 8 is a drawing illustrating the process of cell-free protein synthesis according to one embodiment of the present invention in which glutamic acid decarboxylase and glutamic acid are used.

In Example 3, according to a method for cell-free protein synthesis which is characterized in that pH is controlled by using glutamic acid decarboxylase (GAD) and glutamic acid, about 10,000 gene libraries were expressed and activity of the expressed proteins was screened (FIG. 8).

Figure 9:
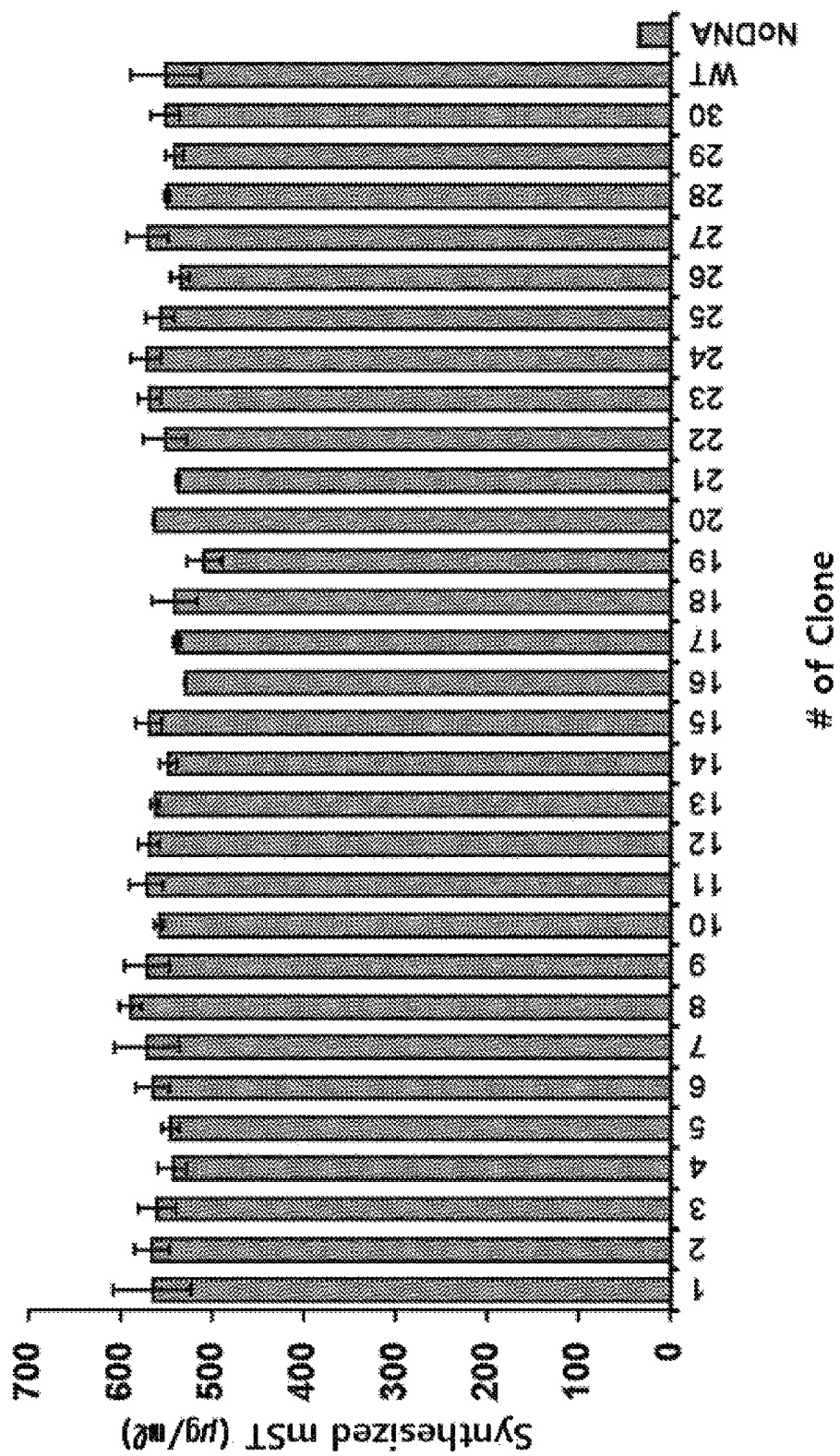
FIG. 9 is a graph illustrating the amount of randomly-selected mutant sialyl transferase which has been synthesized by cell-free protein synthesis according to one embodiment of the present invention. WT represents a wild type sialyl transferase and NoDNA represents a control group in which cell-free protein synthesis is carried out with exclusion of DNA.

As illustrated in FIG. 9, it was confirmed that the mutant sialyl transferases, which have been obtained by cell-free protein synthesis by using the GAD system in which pH is controlled using glutamic acid decarboxylase (GAD) and glutamic acid, are synthesized at the almost same level. Accordingly, it was found that the result of the activity analysis which is obtained by collecting a constant amount of the reaction solution is not based on a difference in the expression amount.

It was also confirmed that the result obtained by applying the sialyl transferase, which has been produced by cell-free protein synthesis using GAD and used without undergoing a separation or purification process, shows the same profile as the result of the activity analysis which has been obtained with the purified sialyl transferase.

As such, it is expected that pH-based enzyme screening which uses a library of proteins synthesized by the cell-free protein synthesis method of an embodiment of the present invention in which pH is controlled by using an amino acid decarboxylase can be suitably carried out.

For establishing a sialyl transferase gene library, random mutation of the codons of threonine (Thr) at the $265^{th}$ amino acid, arginine (Arg) at the $313^{th}$ amino acid, and threonine (Thr) at the $357^{th}$ amino acid of SEQ ID No. 2 was carried out by a PCR method, and the primers used for PCR are shown in Table 1. Among the sites that are expected to be an active site of the sialyl transferase, amino acids at three positions were selected and a randomly mutated gene library was established followed by expression to select a mutant gene of which enzyme activity is enhanced compared to the wild type.

TABLE 1

Primers for establishing sialyl transferase gene library

| Primer name | Start point | Nucleotide sequence (5'->3') |
|---|---|---|
| T7 promoter | Forward | TCGATCCCGCGAAATTAATACGACTCACTATAGG (SEQ ID NO: 3) |
| 1$^{st}$ fragment | Backward | AAAGATAAATTTAGCTTGTTGCACTTC (SEQ ID NO: 4) |
| 2$^{nd}$ fragment | Forward | GAAGTGCAACAAGCTAAATTTATCTTT<u>NNS</u>GG CACG (SEQ ID NO: 5) |
| 2$^{nd}$ fragment | Backward | AGGATGCCCTTTAAAGTAGATTTT (SEQ ID NO: 6) |
| 3$^{rd}$ fragment | Forward | AAAATCTACTTTAAAGGGCATCCT<u>NNS</u>GGTGG TGAAATTAATGACTACATTCTGA (SEQ ID NO: 7) |
| 3$^{rd}$ fragment | Backward | TGAACTTGCAACACCACCCAC (SEQ ID NO: 8) |
| 4$^{th}$ fragment | Forward | GTGGGTGGTGTTGCAAGTTCA<u>NNS</u>TATTTC (SEQ ID NO: 9) |
| T7 terminator | Backward | CAAAAAACCCCTCAAGACCCGTTTA (SEQ ID NO: 10) |

Figure 10:
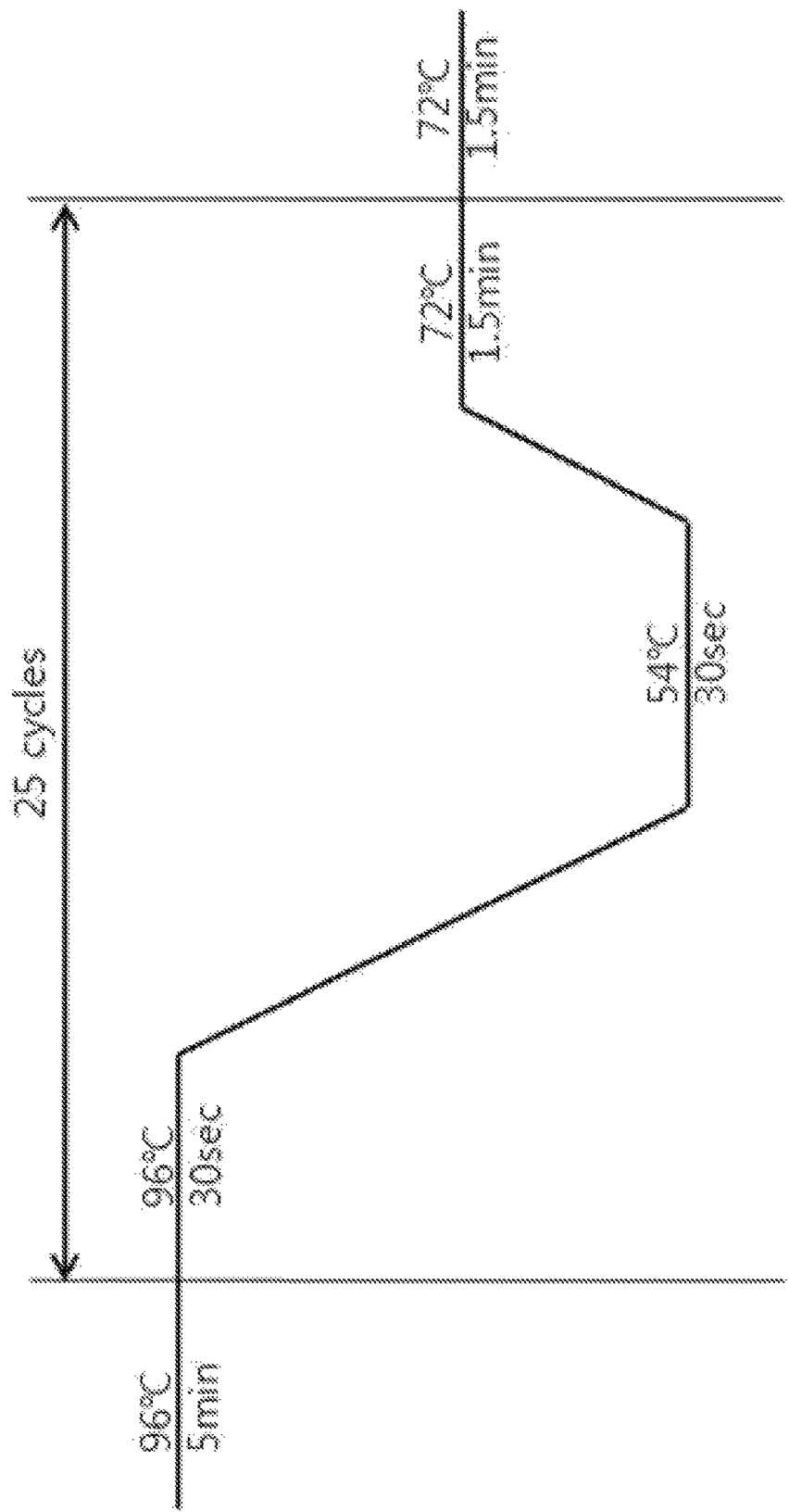
FIG. 10 is a diagram illustrating the conditions for PCR which is used for establishing the gene library of sialyl transferase.

The conditions for carrying out the PCR like temperature and time are shown in FIG. 10. The genes obtained by the PCR were cloned in pIVEX2.3d vector. After obtaining a colony in which each of the above threonine (Thr) at the $265^{th}$ amino acid, arginine (Arg) at the $313^{th}$ amino acid, and threonine (Thr) at the $357^{th}$ amino acid is substituted with a different gene sequence, a gene library was established. By using a colony collector (K3, K biosystems), 10,000 colonies were collected from the library and then inoculated to a 96 well plate in which 200 μl of LB medium is contained. Then, the resulting $10^4$ plates of a 96 well plate were subjected to culture by shaking for 15 hours at 37° C.

The cultured cells were transferred, each in an amount of 1.5 μl, to 26 plates of a 384 well plate in which 23.5 μl of the PCR reaction solution is contained. Thereafter, each gene amplified by the PCR was transferred, each in an amount of 3.0 μl, to a new 384 well plate in which 19.5 μl of the reaction solution for cell-free protein synthesis is contained. The plate was added to a shaker at 30° C. with high humidity and subjected to cell-free protein synthesis reaction for 3 hours.

Immediately after the completion of the cell-free protein synthesis, the reaction solution contained in the sialyl transferase library which has been established in Example 3 was diluted 3 times with 5 mM Tris-Cl (pH 8.5), and then 1.8 μl of the diluted solution was transferred to a 384 well plate, in which 58.5 μl of activity screening solution (5 mM Tris-Cl pH 8.5, 4 mM CMP-NeuAc, 0.4 mM cresol-red, and 4 mM lactose) is added, and incubated for 15 minutes at room temperature. $OD_{600}$ value of the library was measured using a plate reader (Victor 3, PerkinElmer), and a sample showing the highest absorbance was selected. For the transferring step of each of the above processes, an automated liquid handling system (JANUS Automated Workstation, PerkinElmer) was used.

Figure 11:
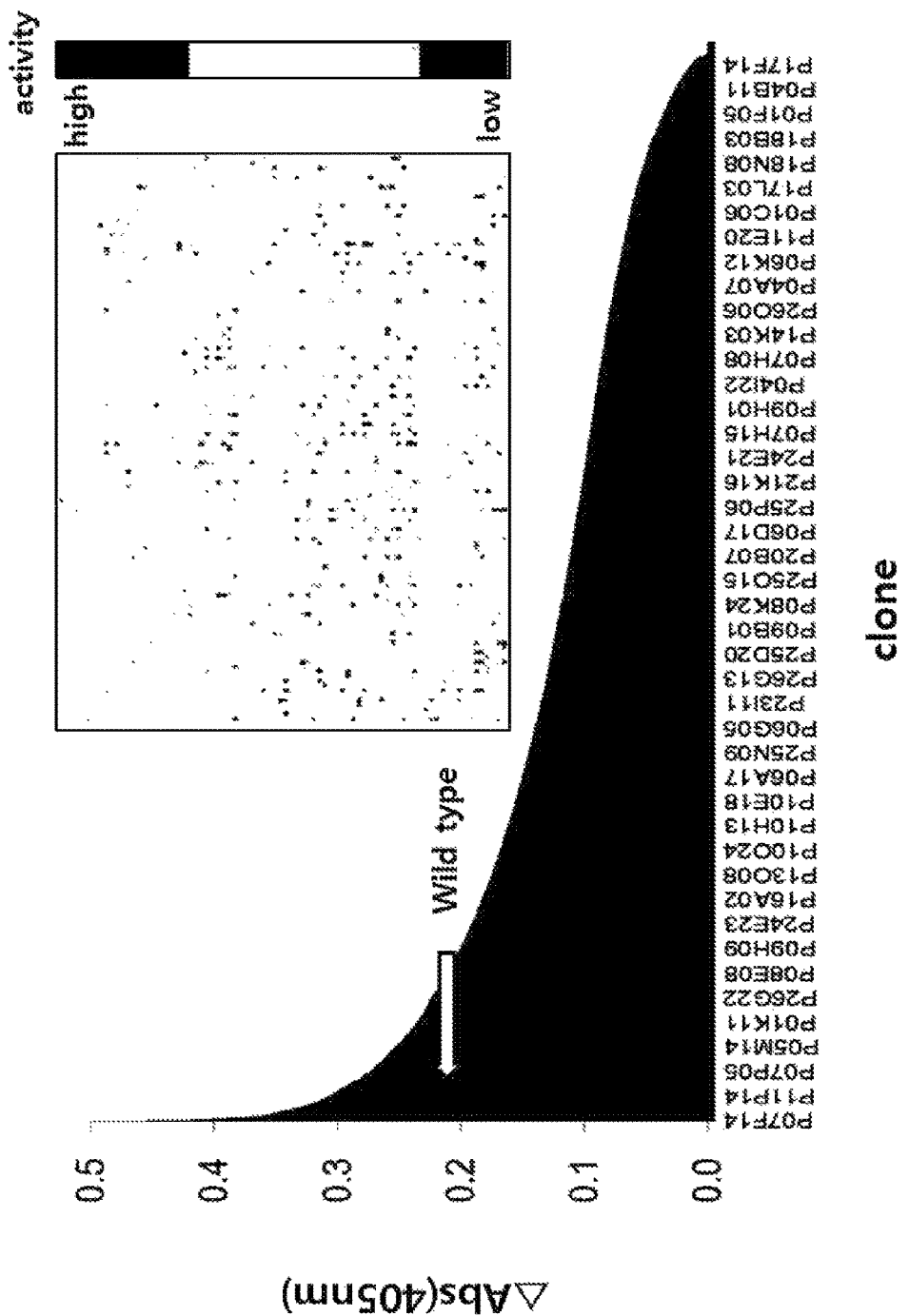
FIG. 11 is a graph illustrating the result of screening the active sialyl transferase, in which the cell-free protein synthesis system is used for the screening.

As shown in FIG. 11, it was able to identify a sialyl transferase with significantly increased activity based on the expression of a sialyl transferase from 10,000 genes and screening of the active type proteins.

What is claimed is:

1. A method for cell-free protein synthesis, comprising: preparing a reaction solution comprising a cell extract, and an energy source comprising adenosine triphosphate, a buffer solution, an amino acid, a gene, and a carbon source; and adding amino acid decarboxylase to the reaction solution to control pH of the reaction solution by removing hydrogen ions that are produced during regeneration of the adenosine triphosphate from the carbon source, wherein the amino acid decarboxylase is glutamic acid decarboxylase having the amino acid sequence of SEQ ID NO: 1, and wherein the glutamic acid at the 89th position of the amino acid sequence of SEQ ID NO: 1 is substituted with glutamine and the amino acids at the 465th position and the 466th position of the amino acid sequence of SEQ ID NO: 1 are deleted.

2. The method for cell-free protein synthesis according to claim 1, wherein the pH is controlled to 6.5 to 8.0.

3. The method for cell-free protein synthesis according to claim 1, wherein the carbon source is at least one selected from the group consisting of monosaccharides, disaccharides, polysaccharides, polyhydric alcohols, and organic acids.

4. The method for cell-free protein synthesis according to claim 1, wherein the carbon source is glucose.

5. A method for cell-free protein synthesis, comprising:
preparing a reaction solution comprising a cell extract, a gene, and an energy source comprising adenosine triphosphate, a buffer solution, an amino acid, and a carbon source; and
adding amino acid decarboxylase to the reaction solution to remove hydrogen ions that are produced during regeneration of the adenosine triphosphate from the carbon source, wherein the amino acid decarboxylase is at least one selected from the group consisting of glutamate decarboxylase EC 4.1.1.15, arginine decarboxylase EC 4.1.1.19, lysine decarboxylase EC 4.1.1.18, aspartate 4-decarboxylase EC 4.1.1.12, valine decarboxylase EC 4.1.1.14, histidine decarboxylase EC 4.1.1.22, tyrosine decarboxylase EC 4.1.1.25, aromatic-L-amino acid decarboxylase EC 4.1.1.28, phenylalanine decarboxylase EC 4.1.1.53, and methionine decarboxylase EC 4.1.1.57.

6. A method for cell-free protein synthesis, comprising:
preparing a reaction solution comprising a cell extract, a gene, and an energy source comprising adenosine triphosphate, a buffer solution, having a concentration of not more than 240 mM, an amino acid, and a carbon source; and
adding glutamic acid decarboxylase to the reaction solution to control pH of the reaction solution to 6.5 or higher by removing hydrogen ions that are produced during regeneration of the adenosine triphosphate from the carbon source,
wherein the glutamic acid decarboxylase has the amino acid sequence of SEQ ID NO: 1, and wherein the glutamic acid at the 89th position of SEQ ID NO: 1 is substituted with glutamine, and the amino acids at the 465th position and the 466th position of SEQ ID NO: 1 are deleted.

* * * * *